United States Patent
Pfenniger

(10) Patent No.: US 9,526,595 B2
(45) Date of Patent: Dec. 27, 2016

(54) METHOD OF PRODUCING A BRUSH FOR THE PERSONAL CARE FIELD

(71) Applicant: TRISA HOLDING AG, Triengen (CH)

(72) Inventor: Philipp Pfenniger, Triengen (CH)

(73) Assignee: TRISA HOLDING AG, Triengen (CH)

( * ) Notice: Subject to any disclaimer, the term of this patent is extended or adjusted under 35 U.S.C. 154(b) by 533 days.

(21) Appl. No.: 13/963,392

(22) Filed: Aug. 9, 2013

(65) Prior Publication Data

US 2013/0319455 A1 Dec. 5, 2013

Related U.S. Application Data

(63) Continuation of application No. 12/734,189, filed as application No. PCT/EP2008/008965 on Oct. 23, 2008, now Pat. No. 8,540,918.

(30) Foreign Application Priority Data

Oct. 24, 2007 (EP) .................................... 07020803

(51) Int. Cl.
*B29C 45/14* (2006.01)
*A61C 15/02* (2006.01)
(Continued)

(52) U.S. Cl.
CPC .................. *A61C 15/02* (2013.01); *A46B 3/18* (2013.01); *A46B 7/04* (2013.01); *A46D 3/005* (2013.01);
(Continued)

(58) Field of Classification Search
None
See application file for complete search history.

(56) References Cited

U.S. PATENT DOCUMENTS 4,691,404 A * 9/1987 Tarrson .................... A46B 3/18
15/144.1
5,283,924 A * 2/1994 Kaminski .............. A46B 9/005
15/167.1
(Continued)

FOREIGN PATENT DOCUMENTS

DE 101 62 998 A1 7/2003
DE 10328445 * 1/2005
(Continued)

OTHER PUBLICATIONS

Machine English translation of DE102006057241 from www.espacenet.com.*
(Continued)

*Primary Examiner* — Edmund Lee
(74) *Attorney, Agent, or Firm* — Oliff PLC

(57) ABSTRACT

The wire of the interdental treatment part is inserted into a shaft opening of the injection molding tool, preferably into a strip of the injecting molding tool such that said treatment part projects with a mounting section thereof into a cavity connected to the shaft opening. Preferably, a first cavity section is configured is configured on the strip, and a second cavity section is configured on a cavity body, to with the strip abuts at least during the injection molding process. After injection of plastic into the cavity, and after the at least partial curing thereof, the handle part thus formed is moved by a distance in the direction against the cavity along with the interdental treatment part, and the handle part is removed from the opened injection molding tool.

5 Claims, 6 Drawing Sheets

(51) Int. Cl.
| | |
|---|---|
| A46B 3/18 | (2006.01) |
| A46B 7/04 | (2006.01) |
| A61C 15/00 | (2006.01) |
| A46D 3/00 | (2006.01) |
| B29C 45/16 | (2006.01) |
| B29C 45/27 | (2006.01) |
| B29L 31/42 | (2006.01) |
| B29C 45/26 | (2006.01) |
| B29C 45/37 | (2006.01) |

(52) U.S. Cl.
CPC ......... *A61C 15/00* (2013.01); *B29C 45/14426* (2013.01); *B29C 45/162* (2013.01); *B29C 45/1671* (2013.01); *B29C 45/2711* (2013.01); *A46B 2200/108* (2013.01); *B29C 45/2673* (2013.01); *B29C 45/37* (2013.01); *B29L 2031/425* (2013.01)

(56) References Cited

U.S. PATENT DOCUMENTS

| | | | | |
|---|---|---|---|---|
| 5,435,033 | A | | 7/1995 | Millner |
| 5,488,751 | A | * | 2/1996 | Gekhter ............... A46B 5/00 132/321 |
| 5,682,911 | A | | 11/1997 | Harada |
| 5,882,584 | A | * | 3/1999 | Tsurukawa ............... A46B 3/18 420/43 |
| 5,934,295 | A | * | 8/1999 | Gekhter ............... A46B 7/04 132/309 |
| 6,158,444 | A | * | 12/2000 | Weihrauch ............. A61C 15/02 132/200 |
| 2005/0032019 | A1 | | 2/2005 | Han et al. |
| 2010/0024839 | A1 | | 2/2010 | Kalbfeld et al. |
| 2010/0307529 | A1 | * | 12/2010 | Schwab ............... A45D 33/18 132/218 |
| 2014/0178650 | A1 | * | 6/2014 | Schnurr ............... B29C 45/164 428/172 |

FOREIGN PATENT DOCUMENTS

| | | | |
|---|---|---|---|
| DE | 10354774 | * | 6/2005 |
| DE | 10 2006 057 241 A1 | | 8/2007 |
| EP | 0 800 781 A2 | | 10/1997 |
| EP | 1 743 547 A1 | | 1/2007 |
| JP | 09327334 | * | 12/1997 |
| JP | A-09-327334 | | 12/1997 |
| JP | A-2000-197520 | | 7/2000 |
| WO | WO 00/56185 A1 | | 9/2000 |
| WO | WO 2009/150964 | * | 12/2009 |

OTHER PUBLICATIONS

European Search Report issued in European Patent Application No. EP 07 02 0803 on Apr. 1, 2008 (with translation).
European Search Report issued in European Patent Application No. EP 07 02 0803 on Jun. 12, 2008 (with translation).
International Search Report issued in International Application No. PCT/EP2008/008965 on May 20, 2009 (with translation).
International Preliminary Report on Patentability issued in International Application No. PCT/EP2008/008965 on May 11, 2010 (with translation).

* cited by examiner

METHOD OF PRODUCING A BRUSH FOR THE PERSONAL CARE FIELD

CROSS-REFERENCE TO RELATED APPLICATIONS

This is a Continuation of application Ser. No. 12/734,189 filed Apr. 23, 2010, now U.S. Pat. No. 8,540,918, which in turn is a National Phase of PCT/EP2008/008965, filed on Oct. 23, 2008, which claims foreign benefit of EP 07020803.8, filed Oct. 24, 2007. The disclosure of the prior applications is hereby incorporated by reference herein in its entirety.

BACKGROUND

The present invention relates to a method of producing a tooth-cleaning device having an interdental treatment part, to a tooth-cleaning device, to a wire for an interdental treatment part, and to a tooth-cleaning device.

For the purpose of cleaning spaces between the teeth, in addition to toothpicks or dental floss, use is also made of tooth-cleaning devices having exchangeable interdental treatment parts, e.g. in the form of a treatment head borne by a stem. Tooth-cleaning devices having exchangeable interdental treatment parts have the advantage that the handle with the fastening element can be used for a number of applications, while only the interdental treatment part need be replaced.

As an alternative, it is also possible for the interdental treatment part to be connected to the handle in a non-releasable manner during production. U.S. Pat. No. 4,691,404 and U.S. Pat. No. 5,882,584 disclose tooth-cleaning devices in which the interdental treatment part is connected to the handle in a non releasable manner. For the purpose of anchoring the interdental treatment part, the wire stem of the latter is preferably encapsulated by injection molding. Alternative anchoring methods are constituted by the stem being adhesively bonded in a blind hole of the handle or by the stem being anchored by means of ultrasound or thermal action.

A tooth-cleaning device having an exchangeable interdental treatment part is known, for example, from DE A 101 62 998. This has a handle which can accommodate an interdental treatment part. The stem of the interdental treatment part can be introduced in the longitudinal direction of the handle. A fastening element is connected to the handle in a pivotable manner. Pivoting the fastening element into the closed state results in the stem of the interdental treatment part being bent and fixed.

Further tooth-cleaning devices are known from U.S. Pat. No. 5,283,924, EP 1 743 547 and U.S. Pat. No. 5,934,295. In the case of the tooth-cleaning devices which are known from these documents, the stem of the interdental treatment part is clamped in a similar manner in each case, for example by way of a cap which is fitted over the handle. In the closed state, the fastening element clamps the stem of the interdental treatment part tight.

The stem usually comprises a wire made of two twisted strands, and the stem has a diameter of approximately 0.48 mm to 0.75 mm. For the purpose of cleaning narrow spaces between the teeth, it is necessary to use a wire of relatively small diameter and thus a stem of relatively small diameter. This gives rise to the problem of it no longer being possible to use known handles for interdental treatment parts or of it no longer being possible for the interdental treatment part to be fixed securely between the moveable fastening element and the handle. A further problem with relatively small stem diameters resides in the reduced resistance to fracturing in the case of alternating bending, which inevitably occurs when use is made of interdental treatment parts.

SUMMARY

It is an object of the present invention to provide a method which makes it possible to produce a tooth-cleaning device which has an interdental treatment part and improved alternating-bending behavior, and also to provide a corresponding tooth-cleaning device. The intention is also to provide a wire of specific composition which is particularly suitable for a stem of an interdental treatment part, and also a tooth-cleaning device having an interdental treatment part which, by virtue of a thin wire diameter, is suitable for narrow spaces between the teeth and can nevertheless be fixed securely on a handle.

This object is achieved according to the invention by a method of producing a tooth-cleaning device having an interdental treatment part, by a tooth-cleaning device, by a wire for an interdental treatment part, and by a tooth-cleaning device.

Preferred further embodiments of the invention are described herein.

For implementing the method according to the invention, and for tooth-cleaning devices and interdental treatment parts according to the invention, use is preferably made of a wire that consists of a steel which contains carbon, silicon, sulfur, chromium, nitrogen, iron, less than 2% by weight of manganese and between 7 and 12% by weight of nickel.

A stem aperture serves, on the one hand, for retaining an interdental treatment part and preventing the escape of plastics material injected into a cavity and, on the other hand, as a guide for a displacement movement of the retaining part, produced by means of the plastics material, or handle together with the interdental treatment part. This displacement movement allows straightforward demolding, even when the retaining part or handle has formed on it a depression which forms an annular gap running around the wire. The method according to the invention allows, in particular, the production of a tooth-cleaning device.

In the case of a tooth-cleaning device, the annular gap and the handle, which bounds the latter radially on the outside, ensure that, in the case of alternating bending, the bending radius, in comparison with the bending radius like that which occurs when the wire simply exits out of the handle without any further lateral support, is large or the bending is divided up between two or more bending regions each with a reduced bending angle. This significantly improves the alternating-bending behavior and thus the service life.

The fastening element in the closed state and the handle as counterpart may fix the interdental treatment part in the tooth-cleaning device. Since the wire from which the stem is made is guided at least in a doubled arrangement over a portion of the stem, pulling out can be prevented. The portion with the wire guided at least in a doubled arrangement allows the interdental treatment part according to the invention to be fixed securely on handles and fastening elements which are provided for interdental treatment parts having a stem made of relatively thick wire. The interaction of a free end of the wire from which the stem is made with a stop surface of the fastening element in the closed state and/or of the handle prevents the interdental treatment part from being pulled out. The free end of the wire here acts like a barb.

The advantages mentioned also apply to interdental treatment parts which are anchored in a handle or a retaining part in a non-releasable manner preferably by means of encapsulation by injection molding.

In particularly preferred embodiments, the wire from which the stem of the interdental treatment part is made is bent over to give two strands, which are twisted. The wire portion preferably consists of a steel which contains iron, carbon, silicon, manganese, sulfur, chromium, nitrogen and nickel and is provided with a coating. In the case of further preferred embodiments, the coating of the wire or of the strands, during use of the tooth-cleaning device, is at least partially dissolvable in water or saliva, and releases active substances in the process, or is designed as a matrix for releasable active substances. Water-soluble, extrudable thermoplastic polymers are preferably used for this purpose.

BRIEF DESCRIPTION OF THE DRAWINGS

The invention will be explained more specifically hereinbelow with reference to exemplary embodiments which are illustrated in detail form, and in part schematically, in the drawing, in which, purely schematically.

DETAILED DESCRIPTION OF THE EMBODIMENTS

Figure 1:
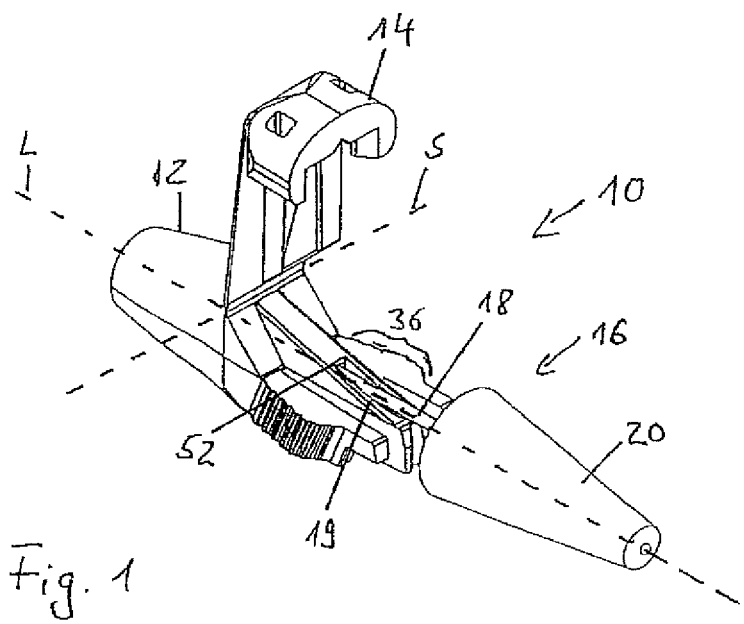
FIG. 1 shows a perspective view of a tooth-cleaning device according to DE A 101 62 998 of the prior art in the open state.

FIG. 1 shows, by way of example, a perspective view of a tooth-cleaning device 10, which is known from DE A 101 62 998. What is said hereinbelow also applies analogously to other tooth-cleaning devices, for example from U.S. Pat. No. 5,283,924, EP 1 743 547 and U.S. Pat. No. 5,934,295 cited in the introduction, which are likewise provided with a moveable fastening element 14 for fixing a stem 18 of a interdental treatment part 16. These documents are added for reference. A partially shown handle 12 defines a longitudinal axis L and has the fastening element 14, which in the present case is pivotable and can be pivoted about a pivot axis S, which is designed in the form of a film hinge. The fastening element 14 is shown in the open state.

The interdental treatment part 16 has a known stem 18 and a treatment head 20 borne by the same. The treatment head 20 is shown as a brush in FIG. 1. It is also possible, however, for the treatment head 20 to be designed in the form of any other desired element for cleaning the spaces between the teeth. An introduction portion 36 of the known stem 18 can be introduced, in the direction of the longitudinal axis L of the handle 12, into an introduction groove 19 of the handle 12 and moved into a blind hole 52. Pivoting the fastening element 14 into the closed state causes the known stem 18 to be bent at right angles and fixed on the handle 12. In respect of construction and functioning, reference is made expressly to DE-A-101 62 998, and the disclosure thereof is hereby added for reference.

Figure 2:
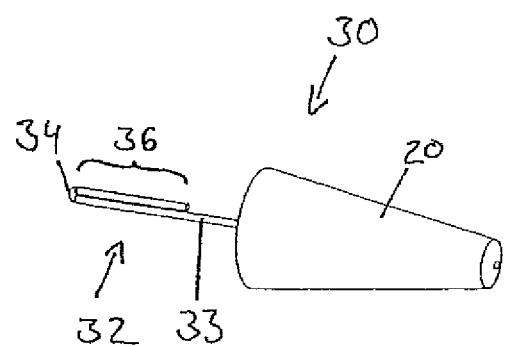
FIG. 2 shows a perspective view of an interdental treatment part according to the invention for a tooth-cleaning device according to the invention.
Figure 3:
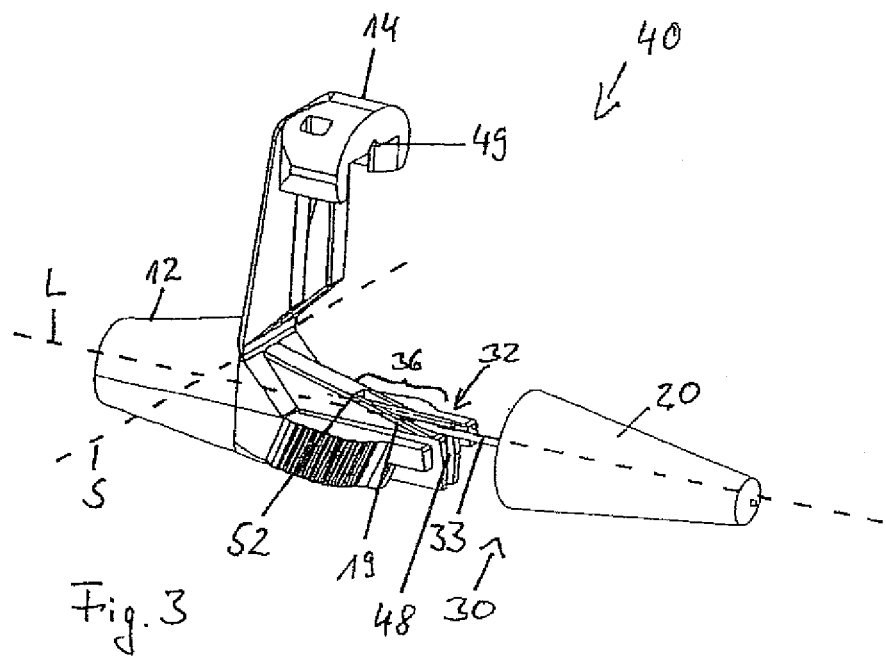
FIG. 3 shows a perspective view of a tooth-cleaning device according to the invention having an exchangeable interdental treatment part according to the invention introduced therein with its stem straight.
Figure 4:
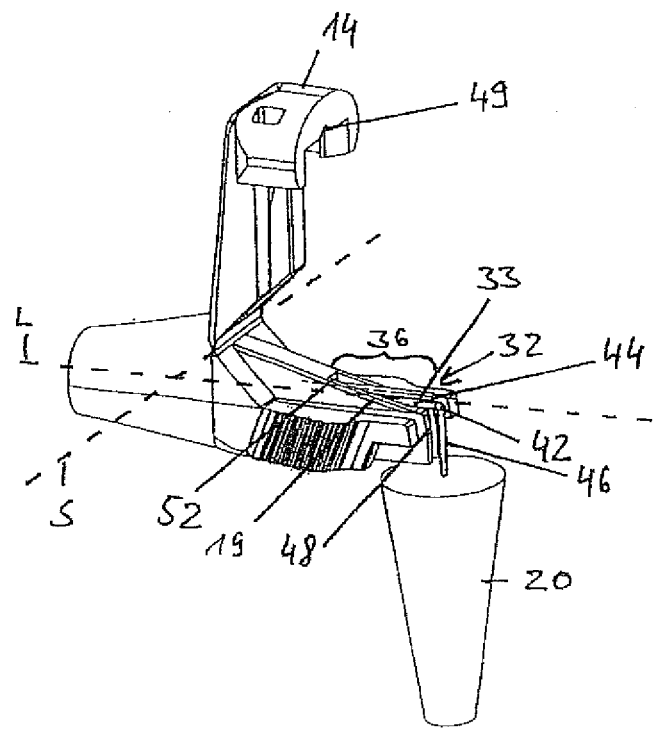
FIG. 4 shows a further perspective view of the tooth-cleaning device according to the invention according to FIG. 3 with an interdental treatment part according to the invention introduced therein with its stem bent.
Figure 5:
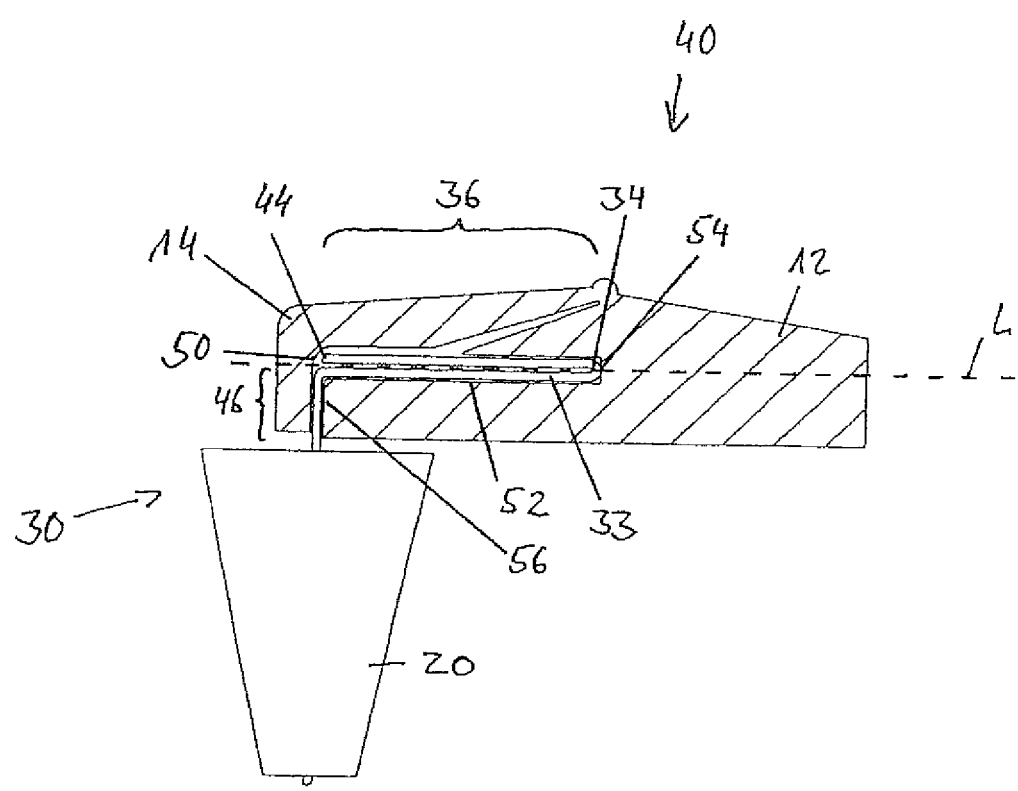
FIG. 5 shows a longitudinal section through the tooth-cleaning device according to FIGS. 3 and 4 having an interdental treatment part according to the invention introduced therein, with its stem bent, in the closed state.

FIG. 2 shows a perspective view of an interdental treatment part 30 according to the invention for a tooth-cleaning device 40 (see also FIGS. 3 to 5). The interdental treatment part 30 according to the invention allows the use of handles 12 and fastening elements 14, which are provided for interdental treatment parts 16 with a known stem 18. The interdental treatment part 30 according to the invention has a treatment head 20, designed in the form of a brush, and a stem 32. The stem 32 is made from wire 33 which has a smaller diameter than the wire of the stem 18 of the known interdental treatment part 16. An end portion of the wire 33 which is directed away from the treatment head 20 is folded over through an angle of greater than 90°, preferably through an angle of between 160° and 180°, usually preferably through 180°. The wire 33 thus forms a bent-over end 34 of the stem 32. The length of the bent-over end portion of the wire 33 defines the length of the portion 36, which is guided in a doubled arrangement with wire 33 and also forms the introduction portion 36. The introduction portion 36 is introduced into the handle 12 in the open state of the fastening element 14.

In FIG. 3, the interdental treatment part 30 according to the invention has been introduced, between the fastening element 14 in the open state and the handle 12, into the introduction groove 19 of the handle 12 in the direction of the longitudinal axis L. The introduction groove 19 merges into a blind hole 52 (see also FIG. 5). The introduction portion 36 is located, at least in part, in the blind hole 52 and butts, by way of the bent-over end 34, at least more or less against the base 54 of the blind hole 52. The interdental treatment part 30 can thus be introduced in a secure and well-defined manner into the handle 12. In addition, the interdental treatment part 30 is retained when the fastening element 14 is located in the open state, and it allows the fastening element 14 to be pivoted into the closed state without the interdental treatment part 30 needing to be held in a hand. The treatment head 20 projects beyond the handle 12 along the longitudinal axis L.

FIG. 4 shows the tooth-cleaning device 40 according to the invention once the fastening element 14, by virtue of being pivoted about the pivot axis S, has been transferred into the closed state and then into the open state again. By virtue of the fastening element 14 being closed, the stem 32 was bent through at least more or less 90°, preferably between 60° and 90°, over a bending portion 42, which is located between the introduction portion 36 and the treatment head 20. The treatment head 20 is thus oriented in a direction at least more or less at right angles to the longitudinal axis L of the handle 12. A free end 44 of the wire 33 of the stem 32 is located at the bending portion 42, and therefore the length of the introduction portion 36 of the stem 32 corresponds essentially to the length between the bent-over end 34 and the bending portion 42. The free end 44 comprises the two ends of the twisted strands. A stem portion 46 between the bending portion 42 and the treatment head 20 is then located in an end groove 48 of the handle 12. The end groove 48 runs at right angles to the introduction groove 19 and thus at right angles to the longitudinal axis L. The fastening element 14 has a groove which complements the end groove 48. If the fastening element 14 is located in the closed state, then the end groove 48 and the complementary groove 49 form a channel 56 through which the stem portion 46 is guided (see also FIG. 5).

FIG. 5 shows a longitudinal section through a tooth-cleaning device 40 according to the invention. The fastening element 14 is located in the closed state. The bending portion 42 has been bent through more or less 90° and the treatment head 20 is oriented in a direction running at right angles to the longitudinal direction L. The introduction portion 36 and the stem portion 46 are clamped in, at least in part, between the handle 12 and the fastening element 14. It is only the doubled arrangement according to the invention exhibited by the wire 33 in the introduction portion 36 which allows the introduction portion 36 to be clamped firmly between the handle 12 and the fastening element 14 which are formed for known stems 18.

The free end 44 of the wire 33 interacts with a stop surface 50. The stop surface 50 is formed by the base of the complementary groove 49. The interdental treatment part 30 is thus fixed according to the invention between the handle 12 and fastening element 14. The interdental treatment part 30 is prevented from sliding out by virtue of the free end 44 interacting with the stop surface 50. The precise position of the free end 44 in relation to the circumferential direction of the stem 32 is of no significance. There is no need for a user, when introducing the interdental treatment part 30 into the handle 12, to be mindful of the rotary position of the stem 32.

The introduction groove 19 and the blind hole 52 facilitate the introduction of the interdental treatment part 30 according to the invention. The doubled introduction portion 36 interacts with the blind hole 52 precisely in the manner of the introduction portion 36 of a known stem 18 of greater thickness. This ensures that the interdental treatment part 30 according to the invention is retained in the handle 12 until it is fixed, by the fastening element 14 in the closed state, between the handle 12 and fastening element 14. In order to allow for manufacturing-induced length tolerances of the stem 18, it is proposed to provide an amount of play between the free end 44 of the wire 33 and the stop surface 50. This amount of play is preferably smaller than 3 mm, further preferably smaller than 1 mm.

By virtue of the free end 44 interacting with the stop surface 50, it is possible, in a further embodiment of the tooth-cleaning device according to the invention, which is not shown, for a different handle to be designed with a different fastening element such that the stem 32, is not bent in the closed state of the different fastening element and the treatment head 20 is oriented in the direction of the longitudinal axis L. The interdental treatment part 30 according to the invention is nevertheless fixed securely by virtue of the free end 44 interacting with the stop surface 50.

In a further embodiment which is not shown, it is also possible for the stop surface 50 to be formed on the handle 12 itself. Of course, the stop surface 50 may merely be formed by some other element of the handle 12 or of the fastening element 14. The angle of the bent-over wire 33 together with the blind hole 52 or the introduction geometry ultimately defines the position of the stop surface 50; or these elements are directly dependent on one another.

The closing mechanism of the fastening element 14 on the handle 12 and further embodiments of handles and fastening elements which are suitable for a tooth-cleaning device 40 according to the invention are described in DE-A-101 62 998. Furthermore, the interdental treatment part 30 according to the invention may also be used in handles which are disclosed, for example, in U.S. Pat. No. 5,283,924, EP 1 743 547 and U.S. Pat. No. 5,934,295.

By virtue of the wire 33 being bent over according to the invention, and of the wire interacting with the stop surface 50, it is possible to achieve a massively higher pull-out weight. During the measurement, the handle 12 is held and the treatment head 20 is subjected to pulling action. There are massive differences here in the pull-out weights for identical wire diameters between the straight end and bent-over end. A pull-out weight of 15 N is required as standard. The bent-over end gives rise to pull out weights which are at least 1.5 times, preferably two times, the magnitude required as standard.

The wire 33 of the interdental treatment part 30 according to the invention is preferably produced from a wire portion which is bent over to form two strands. Pre-bundled filaments are introduced in a known manner at the bent end of the two strands of the bent-over wire portion and cut to size. The two strands of the bent-over wire portion are then twisted together. For the twisting, 8 to 20 turns per cm, preferably 10 to 15 turns per cm, are carried out. Following the twisting, the filaments fixed between the strands are profiled, i.e. adapted to an external shape which is optimum for cleaning purposes. This produces a treatment head 20 which is designed in the form of a brush and is borne by a stem 32 which is made from a wire 33 comprising two twisted strands. Of course, the present invention may also be used for alternative treatment heads (for example made of foam, rubber, plastics material, etc.) or stems made from wire with just one strand or more than two strands.

Once the strands have been twisted, for the purpose of producing an interdental treatment part 30 according to the present invention, that end region of the wire 33 which is directed away from the treatment head 20 is folded over. The bending of the wire 33 is preferably carried out as a further, integrated operating step for producing the treatment head 20 once the filaments have been twisted in in the twisting-in machine. In the case of alternative treatment heads 20, the wire 33 can be bent over before or after the treatment head 20 has been fitted on the stem 32. Bending over takes place in a manner analogous to the operation for bending over the wire comprising two twisted strands. This gives rise to an introduction portion 36 of the stem 32 which has a length between 5 mm and 25 mm, preferably between 7 mm and 15 mm, and has its wire 33 guided in a doubled arrangement.

The handle 12 with the pivotable fastening element 14, which is connected to a film hinge, is preferably produced from a non-brittle hard plastics material. If the fastening element 14 forms a separate unit, a hard plastics material is likewise recommended. Outside the mechanism or within the mechanism, in non-functional geometries, the hard component may have further hard or soft plastics-material components molded over it. Examples of hard plastics materials used are polypropylene (PP), polyester (PET), polycyclohexanedimethanol terephthalate (PCT)/acid-modified PCT/glycol-modified (PCT), polyethylene (PE), polystyrene (PS), styrene acrylonitrile (SAN), polymethyl methacrylate (PMMA), acrylonitrile butadiene styrene (ABS), polyoxymethylene (POM) or polyamide (PA), etc., preferably polypropylene (PP). The preferably used polypropylene (PP) has a modulus of elasticity of 1000-2400 N/mm$^2$, particularly preferably of 1300-1800 N/mm$^2$. Soft plastics materials used are polyvinyl chloride (PVC), polyethylene (PE) with a low density (LDPE, low density polyethylene) or a high density (HDPE, high density polyethylene), elastomeric material such as polyurethane (PUR) or, in particular, thermoplastic elastomers (TPE). Use is preferably made of thermoplastic elastomers. The Shore A hardness of the soft component is preferably less than 90. The soft plastics material may perform an additional function for fixing the stem 32 in that the soft plastics material, at least in a sub-region, is in contact with the stem 32 and thus forms a kind of brake. The soft material here preferably forms a narrowing region in order to maximize the friction in relation to the stem.

The aforementioned materials and the above-described method of producing the interdental treatment part 30, of course, also apply to handles 12 which are connected to the interdental treatment part 30 in a non-releasable manner, preferably by means of the stem 32 being encapsulated by injection molding.

The finished interdental treatment part 30 according to the invention has an overall length of 15 mm to 45 mm, preferably of 25 mm to 35 mm. The treatment head 20 is between 8 mm and 20 mm in length, preferably between 10 mm and 16 mm. The external diameter of the treatment head 20 is between 1 mm and 7 mm, preferably between 2 mm and 5 mm. The bristle tips of a treatment head 20 designed in the form of a brush may form a cylindrical or conical lateral surface or one which undulates as desired. In particular polytrimethylene terephthalate (PTT), polyamide (PA) or polyester (PE), preferably polyamide (PA), is suitable as bristle material for an interdental treatment part 30 according to the invention designed in the form of a brush. The bristles comprise filaments with a diameter between 1 mil and 6 mils, preferably between 1.5 mils and 4 mils, particularly preferably 2.5 mils (where 1 mil=0.0254 mm).

In addition to the interdental treatment parts 30 with a straight stem 32 which are bent, it is likewise possible to use interdental treatment parts 30 which are introduced into an identical, or similar, fastening mechanism, but have already been bent over in a bending portion 42 prior to being introduced into the mechanism. According to the invention, in addition to the stems 32 with an end region which is bent over once, it is also possible to use stems 32 which are made from a wire 33 which is bent a number of times, that is to say where, in the introduction portion 36, the wire has more than a doubled arrangement. It is thus possible for the wire, in the introduction portion, to be guided, for example, in a trebled arrangement. It may then be, for example, in the form of a Z in the introduction portion 36.

The inventive idea may likewise be provided for other brushes which are used for body-care purposes and benefit from relatively small stem diameters. An example which may be mentioned here is that of mascara brushes.

The strand-forming wire portion, on which the production of the interdental treatment part 30 is based, has a pre-twisting diameter of preferably smaller than or, at most, equal to 0.25 mm. The overall diameter of the wire 33 comprising one or more twisted strands, together with the coating, is preferably less than 0.47 mm.

The wire 33 or the wire portion preferably consists of steel which contains iron (Fe), carbon (C), silicon (Si), manganese (Mn), sulfur (S), chromium (Cr), nickel (Ni) and nitrogen (N). The manganese content is preferably smaller than 2% by weight and the nickel content is preferably between 7 and 12% by weight. It is also possible to use nickel-free steels, as are described in EP 1 470 765. It is likewise possible to use steels such as those described in EP 0 800 781. Explicit reference is hereby made to these two documents.

It is preferable for the carbon content of the steel to be between 0.03 and 0.15, in particular between 0.03 and 0.07, percent by weight, for the silicon content to be between 0.3 and 0.6, in particular between 0.3 and 0.4, percent by weight, for the sulfur content to be smaller than 0.01 percent by weight, for the chromium content to be between 16 and 19 percent by weight and for the nitrogen content to be between 0.02 and 0.05 percent by weight, the proportions by weight as manganese and nickel having been given above. However, other known steel alloys, or the combination of different proportions by weight of the customary components of steel, are also possible, and a stable and flexible stem 32 for an interdental treatment part 30 according to the invention can therefore be produced therefrom. These alloys, at the same time, mean that the twisting in process can be carried out cost effectively and the wire can then be bent in accordance with FIG. 2.

The wire 33 or the wire portion is preferably coated with one or more layers. Electrically insulating coats, for example polyurethane (PUR), are particularly well-suited for coating purposes. In addition, coatings made of polytetrafluoroethylene (PTFE)/Teflon are also well-suited. Carrier materials which, during use of the tooth-cleaning device 40, partially dissolve, for example under the action of saliva or water, and release, in particular, active substances in the process or indicate the degree of use of the interdental treatment part 30 or serve as a carrier matrix for active substances which are to be released constitute further options for coatings. In addition to providing for careful cleaning, these coatings can be also be used to adapt the coefficient of friction between the stem 18 and handle 11 or the fastening element 14.

Layer thicknesses of the coatings are usually smaller than 20 μm, and are preferably in the region between 5 μm and 10 μm.

The coating serves as electrical insulation and possibly as a sliding surface. The electrical insulation prevents so-called galvanic shock when metal comes into contact with the tooth. In the case of nickel-containing steels, the coating additionally prevents a possible allergic reaction since the coating minimizes, or even prevents, nickel escaping.

As active substances which are introduced into the coating, use may be made of ingredients with a toothpaste-like action, for example sorbitol, flavorings, hydrated silica, sodium lauryl sulfate, triclosan, glycerin, sodium saccharine, propylene glycol, disodium phosphate, aluminum oxide, trisodium phosphate, monofluorophosphate, sodium fluoride, betaines, titanium dioxide, cellulose gum, tetrasodium pyrophosphate, creatine, zinc sulfate, amine fluoride, sodium fluoride (NaF) or the like.

It is also possible to produce antibacterial effects with the aid of ingredients such as sodium bicarbonate, citric acid, phosphoric acid, sodium carbonate, potassium carbonate, sodium perborate, sodium hexametaphosphate, sodium benzoate, sodium stearate and/or similar substances.

Additives such as glucose, maltodextrine, magnesium stearate, flavoring, saccharine, microcrystalline cellulose and similar means which dye the plaque, and thus indicate the cleaning success, may likewise be used, as can means for bleaching the teeth, for example hydrogen-peroxide-containing substances.

Combinations of compatible active substances which are mentioned above are likewise suitable for coating purposes.

As a carrier material for the active substances which cannot be applied directly to the wire 33 or wire portion, it is possible to use, for example, biodegradable substances based on starch or other suitable plastics materials which do not react chemically with the ingredients. For example a washer-soluble synthetic resin based on polyethylene-oxide polymers and forming a matrix for an active substance or polyethylene glycol (PEG) is also suitable. Of course, other water-soluble, extrudable thermoplastic materials may also be used as carriers for active substances.

The various coatings may be applied by means of different methods. One option is constituted by the coating being molded on, the plastics-material sheath being applied to the wire or wire portion by means of injection molding. A further method is the extrusion of the coating. The wire is drawn through a die and, at the same time, the coating is applied to the wire by means of extrusion.

The coatings, that is to say the coats applied in layers, and also the other substrates may be dyed. The dying, like the coating, is carried out preferably using non-toxic, saliva-resistant and non-migrating, food-compatible dyes/materials.

It is possible for the wire to be provided with a number of coatings. This can be done in one or more sequential processes. For example, the wire may have, over an inner coating made of a non-water-soluble layer (for example polyurethane or polytetrafluoroethylene), an outer, water-soluble layer (for example polyethylene-oxide polymers or polyethylene glycol) with active substances contained therein.

The wire with the above-described composition and also the above-described coating options for wires can also be used in any other desired tooth-cleaning devices. In particular, it is also conceivable to use the wire in conjunction with plastics-material parts which are molded directly on the stem 32, for example directly molded-on grips or grip parts.

Figure 6:
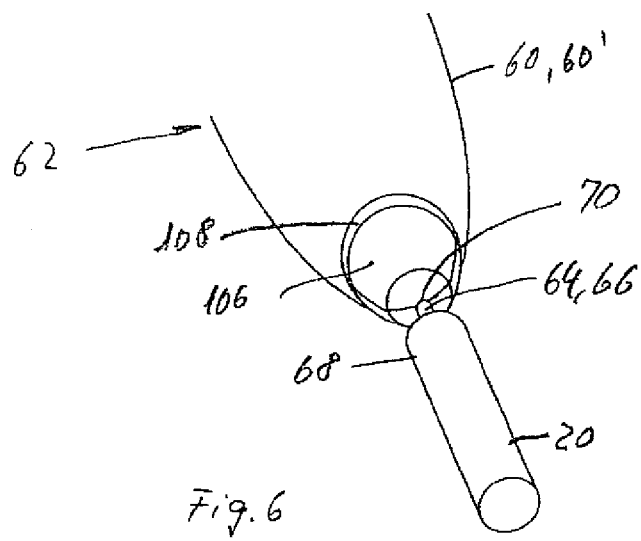
FIG. 6 shows a perspective illustration of part of a tooth-cleaning device according to the invention in the case of which the wire of the interdental treatment part has been encapsulated by injection molding in a plastics material of the handle.

FIG. 6 shows a part of a handle 60 of a further tooth-cleaning device 62, wherein the wire 66, which forms the stem 64, is connected in a non-releasable manner to the handle 60 made from plastics material. The wire 66, which bears the treatment head 20 and, together therewith, forms the interdental treatment part 68, preferably consists of the same material, and preferably has the same diameters, as described above. Moreover, the wire 66 may be coated in the same way as disclosed above. In the handle 60, the wire 66 can be bent back, as is shown in FIG. 2, but it is also conceivable for it not to be bent in this way.

The handle 60, in the embodiments shown in FIGS. 6 to 16, is of droplet-like form, wherein two mutually opposite sides are preferably flattened, and this allows the handle 60 to be held reliably by means of the thumb and forefinger. What is said hereinbelow applies analogously if the handle 60 is replaced by a retaining part 60' which is intended to be retained by a handle member in a non-releasable or releasable manner.

In the case of the embodiment which is shown in FIG. 6, the handle 60 is of slightly convex, more or less planar, form, at the location 70 where the wire 66 exits out of the handle 60, wherein the wire 66 exits out of the handle 60 essentially at right angles to the surface thereof.

During the cleaning operation, the interdental treatment part 68, and particularly the wire 66 thereof, are subjected to pronounced stressing at the exit location 70 as a result of the very high incidence of alternating loading, which is accompanied by the risk of a fatigue fracture of the wire 66. If the thin wire, according to the invention, is subjected to alternating loading as occurs during the cleaning of spaces between the teeth, it is possible for the wire 66 to be bent, at the exit location 70, through approximately 80° to 90° with a radius which is usually smaller than 1 mm, in many cases smaller than 0.5 mm. This virtual buckling of the wire, even after a small number of cleaning cycles, for example 3 to 6 cycles, may result in the wire 66 fracturing.

Figure 7:
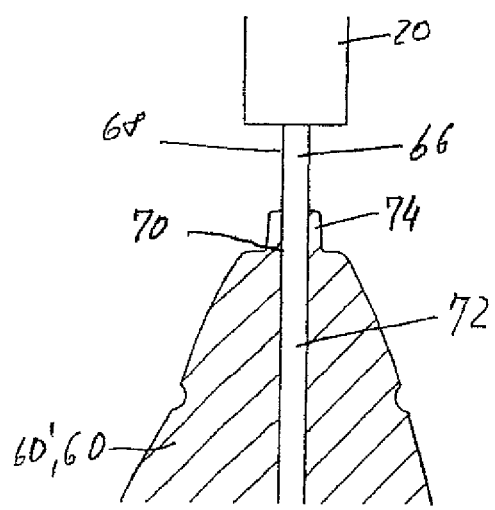
FIG. 7 shows, partly in longitudinal section, a tooth-cleaning device similar to that according to FIG. 6, although the handle has a tubular protrusion enclosing the wire.
Figure 8:
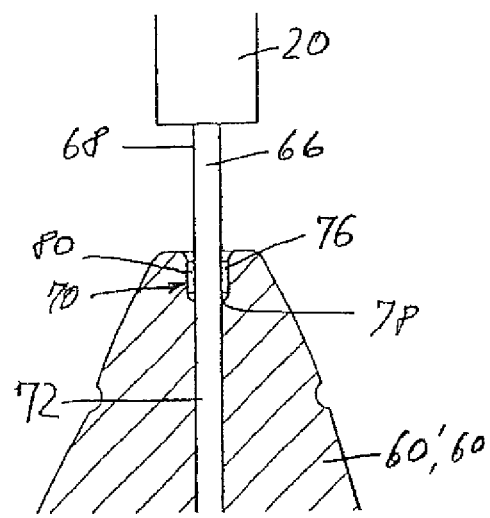
FIG. 8 shows, in the same illustration as FIG. 7, a similar tooth-cleaning device, the handle having a depression at the location where the wire exits.

In order to prevent this, the handle 60 is preferably designed in the manner illustrated in FIGS. 7 and 8. These embodiments prevent the wire from buckling at the exit location by giving rise, during the alternating loading, to a relatively large bending radius of the wire or to a plurality of bending locations with relatively small bending angles.

The wire 66, which bears the treatment head 20 and is formed for example from two twisted strands, runs rectilinearly into the handle 60 and, in a fastening portion 72 located in this handle, is encapsulated by injection molding, and secured, by a plastics material which forms the handle 60. The handle 60 is in the same form as that described in conjunction with the embodiment which is shown in FIG. 6, although in this case a sleeve-like or tubular continuation 74 of the handle 60 encloses the wire 66 at its exit location 70. This sleeve-like or tubular continuation 74 is produced during the injection molding of the handle 60 by virtue of the wire 66 being encapsulated by injection molding in a hard plastics material or soft plastics material, as is disclosed above. The continuation 74, which thus butts against the wire 66, has a much lower bending strength than the rest of the plastics material body of the handle 60. The continuation projects beyond the plastics material body of the handle 60 by a length of approximately 0.5 mm to 4 mm, preferably of 0.8 mm to 1.6 mm. The external diameter of the continuation 74 is approximately 0.4 mm to 1.3 mm, preferably 0.5 mm to 1.1 mm.

As a result of this embodiment with a continuation 74, the wire is guided in a flexible manner at, and adjacent to, the exit location 70. The flexible continuation 74 is likewise subjected to loading during the alternating stressing on the interdental treatment part 68, wherein it bends—to a slight extent—together with the wire and thus forms a kind of crumple zone which increases the bending radius of the wire 66, in relation to the embodiment shown in FIG. 6, to at least 1.2 mm, preferably at least 1.6 mm.

It is also possible for the continuation 74 to taper in the direction of its free end, for example to be conical with an angle preferably between 10° and 40°. The continuation 74 here has at its foot, at the transition into the plastics material body of the handle 60, an external diameter of 0.7 mm to 1.5 mm, preferably of 0.9 mm to 1.2 mm and at its end an external diameter, for example, of 0.4 mm to 0.9 mm, preferably of 0.5 mm to 0.7 mm.

FIG. 8 shows a particularly preferred embodiment of the handle 60 at the exit location 70 which likewise significantly reduces the risk of fatigue fracture to the wire 66 in relation to the embodiment which is shown in FIG. 4. The plastics-material body forming the handle 60 has, at the exit location 70 of the wire 66, a depression 76, at the base 78 of which the wire 66 exits out of the handle 60 and which leaves free an annular gap 80 running around the wire 66. In the event of alternating stressing, the wire is bent only to a slight extent at the base 78 because, in the case of relatively pronounced deflection, the wire 66, at least at the free end region of the depression 76, ends up butting against the handle 60, which gives rise overall to a significantly larger bending radius of at least 1.2 mm, preferably at least 1.6 mm, than is the case in the embodiment according to FIG. 6. It is possible here for the wire 66 to have a smaller bending radius at the base 78, and at the free end region of the depression 76, than therebetween. However, the bending angle at these locations is significantly smaller than the bending angle at the exit location 70 of the embodiment according to FIG. 6 with the same deflection of the treatment head 20.

It is likewise possible here for the depression 76 to widen conically in the direction of its free end and thus for the wire 66 to be provided continuously with increasingly more space in the direction of the free end of the depression 76. The depression 76 here may be designed conically or such that it widens in a trumpet-like manner.

A preferred form of the depression 76 is shown in FIG. 8. The depth of the depression 76, as measured from the free end of the handle 60, enclosing the depression 76, as far as the base 78, is, for example, 0.5 mm to 1.8 mm, preferably 0.6 mm to 1.6 mm. In a central portion, which is circular-cylindrical in the exemplary embodiment shown, the depression 76 has an inside width of 0.4 mm to 1 mm, preferably 0.5 mm to 0.9 mm. At the base 78, following the central portion, the depression 76 narrows in the direction of the wire 66 with a radius of preferably 1.8 mm to 2.2 mm. In the direction of the free end, and following the central portion, the depression 76 widens with a radius, for example, between 0.2 mm and 0.5 mm.

In order to configure the handle 60 itself to be somewhat more flexible, instead of the hard plastics material, in particular polypropylene, which is preferably used, it is also possible to use a mixture of one of the above-specified hard plastics materials and a likewise specified soft plastics material. Use is preferably made, in this case, of a mixture of 60 to 80 percent by volume of polypropylene and 20 to 40 percent by volume of thermoplastic elastomer (TPE). It is also conceivable, for reasons of flexibility, to produce the handle 60 from polyethylene (PE) with a low density (LDPE, low density polyethylene) or a high density (HDPE, high density polyethylene).

Furthermore, it is also possible to produce the handle 60 by means of multi-component injection molding, wherein it is conceivable for the handle 60 at the continuation 74, or at the depression 76, to be made from a soft/elastic plastics material and for at least some of the remaining plastics material body to be made from a hard plastics material, or vice versa. It is also conceivable for the handle, which is otherwise made from a hard plastics material, to be provided in certain regions, in particular in regions where it is held in the hand or by fingers, with a soft plastics material, in order to improve the haptic properties.

In the case of the embodiments which are shown in FIGS. 7 and 8, the handle 60 is axially symmetrical in relation to the wire 66 at the exit location 70, i.e. also in the region of the continuation 74 or of the depression 76. It is also possible to deviate from this symmetry. Furthermore, it is also possible for the handle which has the fastening element 14 and is shown in FIGS. 3 to 5 to be designed, at the exit location of the wire out of the handle 12, in the manner described in conjunction with FIGS. 7 and 8. The same applies to differently constructed handles for retaining interdental treatment parts in an exchangeable manner.

A method according to the invention of producing a tooth-cleaning device having an interdental treatment part as is disclosed in FIGS. 6 to 8 will be explained hereinbelow in conjunction with an injection mold 90 which is suitable for this purpose. The injection mold 90 can be opened and closed—as is generally known. For this purpose, it has two mold halves which, in the closed state, butt against one another in a known manner along a parting surface 92. The closed injection mold 90 bounds at least one cavity 94, but preferably a multiplicity of cavities, into which the plastics material is injected, in the present case for the purpose of forming the handle 60.

For the sake of simplicity, FIGS. 9 to 11, 14 and 16 illustrate only one of the two parts of a clamping bar 96 and of a cavity body 98 of the injection mold 90, these parts being symmetrical to the parting surface 92 in the present case.

Figure 10:
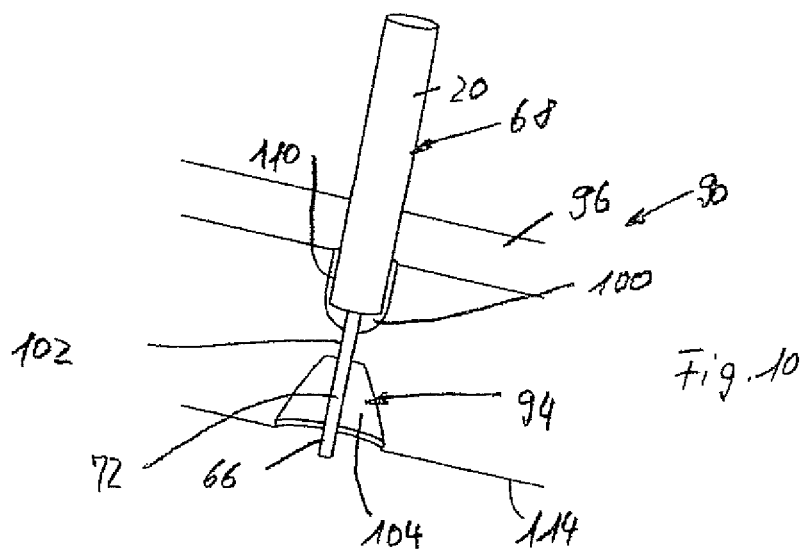
FIG. 10 shows, in the same illustration as FIG. 9, the part of the mold bar with an interdental treatment part inserted therein.
Figure 9:
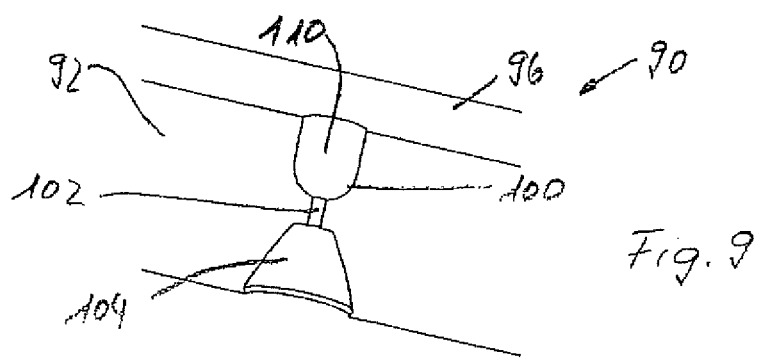
FIG. 9 shows a perspective illustration of part of a bar of an injection mold having a stem aperture and a first cavity portion of a cavity forming mold bar.
Figures 11, 12:
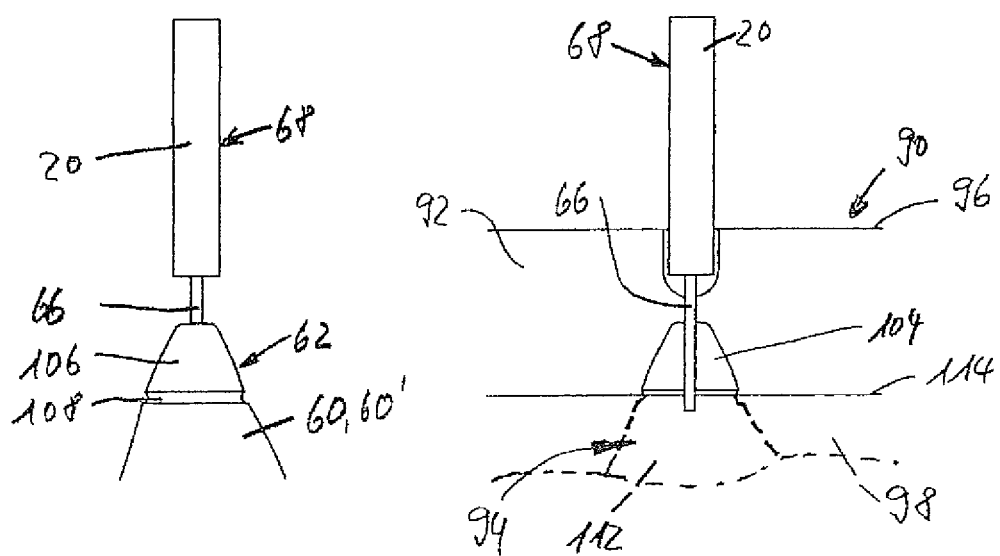
FIG. 11 shows a view of the part of the mold bar according to FIGS. 9 and 10 with the interdental treatment part inserted, the mold bar butting right up against a cavity body of the injection mold.
FIG. 12 shows a view of part of a tooth-cleaning device produced by means of the injection mold according to FIGS. 9 to 11.

The clamping bar 96 according to FIGS. 9 to 11 has a rectangular cross section and an aperture 100 running through it. It is preferable, however, to have a multiplicity of identical apertures 100 in a row one behind the other, in order for it to be possible to produce a corresponding number of tooth-cleaning devices 62 simultaneously. The aperture 100 is symmetrical in relation to the parting surface 92 and has, in a central portion, a stem aperture 102 of which the diameter is coordinated with the diameter of the wire 66 such that, during injection molding, it is not possible for any plastics material to flow through out of the cavity 94 between the stem aperture 102 and the wire 66. Following the stem aperture 102, the aperture 100, forming a first cavity portion 104 of the cavity 94, is formed in a manner corresponding to the shape of the handle 60 in an end region 106 which has the exit location 70. This end region 106 extends, in the example shown, from that end of the handle 60 which is directed toward the treatment head 20 as far as an encircling groove 108, over a length of approximately 3 mm of the handle 60. This length, however, may also be selected to be shorter or longer. Furthermore, following the stem aperture 102, the aperture 100 has, on the side which is directed away from the first cavity portion 104, a widened receiving portion 110 for the treatment head 20 of the interdental treatment part 68. The widened receiving portion 110 is preferably designed such that it can receive with lateral play that part of the treatment head 20 which projects into it, and also the corresponding portion of the wire 66, as can be seen from FIGS. 10 and 11.

For the purpose of producing the handle 60 by means of injection molding, the clamping bar 96 is brought into close-fitting abutment against the cavity body 98. The first cavity portion 104, which is formed on the clamping bar 96, comes into alignment here with a second cavity portion 112, which is formed on the cavity body 98, wherein this second cavity portion together with the first cavity portion 104 forms the cavity 94 for the handle 60.

For the sake of completeness, it should be mentioned that the one part of the groove 108 is formed by the first cavity portion 104 and the other part is formed by the second cavity portion 112. The abutment plane 114, along which the clamping bar 96 and the cavity body 98 butt against one another, thus runs at right angles to the longitudinal direction of the tooth-cleaning device 62, this longitudinal direction coinciding with the wire 66, and approximately centrally through the groove 108, as seen in this longitudinal direction.

With the clamping bar 96 open, the wire 66 of the interdental treatment part 68 is inserted into the stem aperture 100 such that it projects into the cavity 94 by way of its fastening portion 72, which is located at a distance from the treatment head 20. As can be seen from FIG. 11, the wire 66 engages, by way of its fastening portion 72, through the first cavity portion 104 and extends into the second cavity portion 112. With the clamping bar 96 closed, and butting against the closed cavity body 98, the plastics material is injected into the cavity 94, as a result of which the fastening portion 72 of the wire 66 is encapsulated by injection molding and the handle 60 is produced. Following at least partial curing of the injected plastics material, the cavity body 98 and the clamping bar 96 can be opened and the finished tooth-cleaning device 62, i.e. the handle 66 with the interdental treatment part 68 connected thereto in a non-releasable manner, can be removed from the injection mold 90.

Designing the injection mold 90 with a clamping bar 96 which is separate from the cavity body 98 has a number of advantages. For example, the clamping bar 96 can be charged with the interdental treatment part 68, preferably with a multiplicity of interdental treatment parts 68, in a separate position from the cavity body 98. There are advantageously at least two clamping bars 96 present for each cavity body 98, these clamping bars being charged alternately with interdental treatment parts 68, and/or butt against the cavity body 98 for the purpose of producing the handle 60. This allows automated production with very short cycle times made up essentially of the time for injecting the plastics material, the time for partially curing the plastics material and the changeover required for the clamping bars 96, albeit without the time required for unloading and loading the same.

Furthermore, for producing tooth-cleaning devices 62 with the same form of handle 60 but a different diameter of the wire 66, all that is required is to exchange the clamping bar 96 with a stem aperture 102 corresponding to the diameter of the wire 66, while the cavity body 98 can remain in the injection mold.

Using a clamping bar 96 which is separate from the cavity body 98 has the further advantage that, in multi-component injection molding, the changeover from the second cavity portion 112 into a further second cavity portion, into which a second plastics material is injected, can take place by means of the clamping bar 96.

Since an encircling bead of the clamping bar 96, this bead forming the relevant part of the groove 108, engages in this groove 108 of the handle 60 produced, the tooth-cleaning device 62 is retained securely in the clamping bar 96 in order for the handle 60, with the cavity body 98 open, to be removed from the second cavity portion 112.

The interdental treatment part 68 is, or the appropriate number of interdental treatment parts 68 are, thus preferably inserted into an open clamping bar 96 and the clamping bar 96 is closed. The closed clamping bar 96 is then brought into abutment against the cavity body 98, which is already closed or is yet to be closed, and then the plastics material is injected into the cavity 94. As soon as this plastics material has partially cured, i.e. cured to the extent where the handle 60 is dimensionally stable, the cavity body 98 is opened and the still closed clamping bar 96 is removed from the cavity body 98, the movement direction, at least initially, being transverse, preferably at right angles, to the parting surface 92. The handle 60 is thus removed from the second cavity portion 112. The clamping bar 96 is moved into a position remote from the cavity body 98, while, at the same time, a new, loaded clamping bar 96 is brought into abutment against the cavity body 98. In the aforementioned position, the clamping bar 96 is then opened and the finished tooth-cleaning device 62 is removed from it.

Of course, it is also conceivable for the parts of the clamping bar 96 to be formed integrally with the corresponding parts of the cavity body 98. This, however, results in the advantages relating to short cycle times and the ability to exchange just the clamping bar 96 in order to produce tooth-cleaning devices 62 with a different diameter of the wire 66 being lost.

Figure 13:
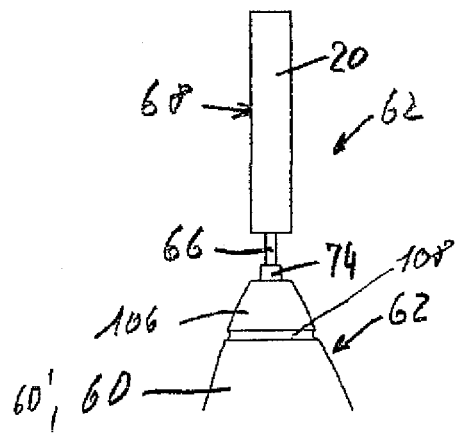
FIG. 13 shows a view of part of the tooth-cleaning device according to FIG. 7 having the tubular handle extension enclosing the wire.
Figure 14:
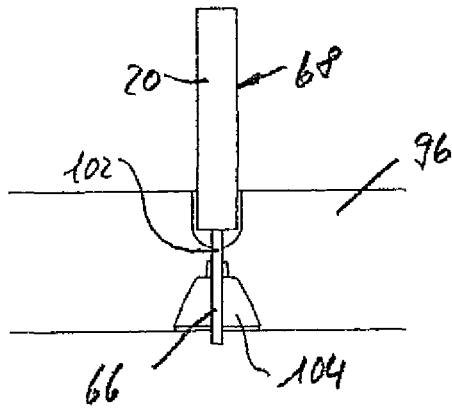
FIG. 14 shows a view of part of the mold bar for producing the tooth-cleaning device according to FIGS. 7 and 13.

FIG. 13 shows a view of part of the tooth-cleaning device 62 according to FIG. 7 with the tubular continuation 74 and FIG. 14 shows, in the same illustration as FIG. 11, the clamping bar 96 which is suitable for producing this embodiment. This clamping bar is designed in a manner which is precisely identical to that described in conjunction with FIGS. 9 to 11, although the first cavity portion 104, in accordance with the shape of the continuation 74, and the stem aperture 102 are of somewhat shorter design. The method of producing this tooth-cleaning device 62 is exactly the same as that described in conjunction with FIGS. 10 to 12.

Figure 15:
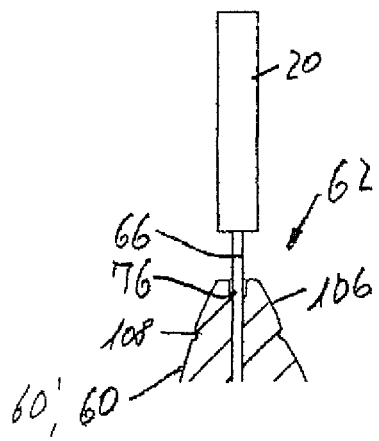
FIG. 15 shows a view of part of the tooth-cleaning device according to FIG. 8 having a depression in the handle at the location where the wire exits.
Figure 16:
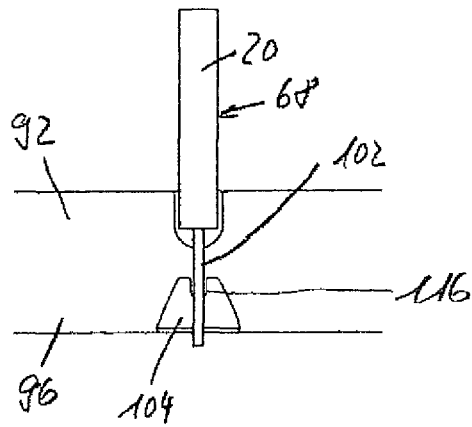
FIG. 16 shows, in the same illustration as FIG. 14, part of a mold bar for producing the tooth-cleaning device according to FIGS. 8 and 15.

For the purpose of producing tooth-cleaning devices 62 as are shown in FIGS. 8 and 15, however, demolding requires a displacement movement of the tooth-cleaning device 62, in the direction of the stem 64, in the direction into the first cavity portion 104, or into the cavity 94. The clamping bar 96 and the cavity body 98 are designed in precisely the same manner as described in conjunction with FIGS. 9 to 11, although, here, the clamping bar 96 has a protrusion 116 which corresponds to the depression 76—see FIG. 8—and projects in the direction into cavity 94. Here too, the clamping bar 96 is loaded with the interdental treatment part 68 in the manner described above. Following the injection molding of the handle 60, once the cavity body 98 has been opened, the clamping bar 96 is removed from its abutment against the cavity body 98 and then opened. The aforementioned displacement movement of the tooth-cleaning device 62, in order to remove the handle 60 from the region of the protrusion 116, takes place either prior to the clamping bar 96 being opened or during the operation of opening this clamping bar. The displacement movement can take place either by virtue of pushing on the treatment head 20 or by virtue of pulling on the handle 60. It is preferred, however, for the displacement movement to be produced by the opening movement of the clamping bar 96 itself in a direction at right angles to the parting surface 92. The shape of the protrusion 116, tapering in the direction of the free end, and the corresponding widening shape of the depression 76 of the handle 60 are used to achieve this.

Of course, a displacement moment can also take place in the embodiments according to FIGS. 9 to 14.

As described above, the bead of the clamping bar 96, this bead engaging in the groove 108, prevents the tooth-cleaning device 62 from dropping out of the clamping bar 96 in an undesired manner. This bead thus forms a kind of anchoring element, although the bead need not necessarily be in uninterrupted form all the way round the circumferential direction. Correspondingly, however, it is also conceivable for the first cavity portion 104 to have an encircling bead-like widened portion which is formed by a groove on the clamping bar 96, and this, in turn, need not necessarily be uninterrupted. Examples of other possible kinds of anchoring elements are grooves or beads running axially or obliquely on the clamping bar 96.

Of course, the treatment head 20 is spaced apart from the fastening portion 72 by such a distance that the aforementioned displacement movement of, for example, not more than 3 mm, but preferably not more than 2 mm, can be executed without the treatment head being damaged by abutment against the clamping bar 96.

The distance thus corresponds at least to the length of the stem aperture 102 and, in the case of a displacement movement being executed, to the distance of the displacement movement in addition.

In order for it to be possible for the displacement movement to be produced by virtue of the clamping bar 96 being opened, the protrusion 116 has, on its radially outer lateral surface, a preferably conical portion with a slope of 10°, preferably at least 20°.

It is also possible, in the manner explained above, for the handle 60 to be designed as a retaining part 60' which is intended to be fastened on a handle member in a non-releasable or releasable manner.

What is claimed is:

1. A method of producing a brush for the personal care field by means of multi-component injection molding with an injection mold comprising at least a clamping bar and a cavity body, the clamping bar defining a first cavity portion of a cavity of the injection mold, and the cavity body defining a second cavity portion of the cavity of the injection mold, the method comprising at least the following steps:
   (a) inserting a stem being made from a wire and bearing a treatment head into a stem aperture of the clamping bar of the injection mold such that a fastening portion of the wire projects into an open cavity of the injection mold;
   (b) closing the injection mold by bringing the clamping bar and the cavity body into abutment such that the first cavity portion and the second cavity portion form a closed cavity of the injection mold;
   (c) injecting a first plastics material into the closed cavity such that the fastening portion of the wire is encapsulated, wherein a handle of the brush is produced and an encircling groove is formed in the handle substantially by means of an encircling bead of the clamping bar;
   (d) opening the injection mold;
   (e) performing, by means of the encircling bead of the clamping bar engaging in the groove of the handle, a changeover from the second cavity portion into a further second cavity portion; and
   (f) injecting a second plastics material into the further second cavity portion.

2. The method as claimed in claim 1, wherein the first plastics material which is injected in step (c) is a hard plastics material for forming the handle of the brush.

3. The method as claimed in claim 1, wherein the second plastics material which is injected in step (f) is a soft plastics material.

4. The method as claimed in claim 1, wherein the brush includes a tooth-cleaning device comprising an interdental treatment part or a mascara brush.

5. The method as claimed in claim 1, wherein steps (d) to (f) are repeated analogously.

* * * * *